United States Patent
Kinast et al.

(10) Patent No.: US 8,328,772 B2
(45) Date of Patent: Dec. 11, 2012

(54) NEEDLE FOR PENETRATING A MEMBRANE (75) Inventors: Peter Kinast, Friolzheim (DE); Kjell Andreasson, Vastra Frolunda (SE); Einar Jorgensen, Hisings Karra (SE); Fredrik Backstrom, Vastra Frolunda (SE)

(73) Assignee: Carmel Pharma AB, Gothenborg (SE)

( * ) Notice: Subject to any disclaimer, the term of this patent is extended or adjusted under 35 U.S.C. 154(b) by 615 days.

(21) Appl. No.: 10/542,823

(22) PCT Filed: Jan. 21, 2004

(86) PCT No.: PCT/SE2004/000070
§ 371 (c)(1),
(2), (4) Date: Jul. 24, 2006

(87) PCT Pub. No.: WO2004/064903
PCT Pub. Date: Aug. 5, 2004

(65) Prior Publication Data
US 2006/0276759 A1 Dec. 7, 2006

Related U.S. Application Data (60) Provisional application No. 60/441,098, filed on Jan. 21, 2003.

(30) Foreign Application Priority Data

Jan. 21, 2003 (SE) .................... 0300155.9

(51) Int. Cl.
*A61M 5/32* (2006.01)

(52) U.S. Cl. ....................................................... 604/274

(58) Field of Classification Search .................. 604/272, 604/273, 274, 264; 163/5
See application file for complete search history.

(56) References Cited

U.S. PATENT DOCUMENTS

| 1,844,342 A | 2/1932 | Berman | |
|---|---|---|---|
| 2,010,417 A | 8/1935 | Schwab | |
| 2,697,438 A * | 12/1954 | Hickey | 604/274 |
| 2,717,599 A * | 9/1955 | Huber | 604/274 |

(Continued)

FOREIGN PATENT DOCUMENTS

AU 200112863 5/2003

(Continued)

OTHER PUBLICATIONS

Taiwan Search Report for Taiwan Patent Application 092106323, dated Mar. 21, 2003 (4 pages).

(Continued)

*Primary Examiner* — Kevin C Sirmons
*Assistant Examiner* — William Carpenter
(74) *Attorney, Agent, or Firm* — Diehl Servilla LLC (57) ABSTRACT

A needle 1 for penetrating a membrane 2, having a pointed end 3 provided with a penetrating tip 4 and with an opening 6 for letting a liquid in and/or out in a main direction 7 which is substantially parallel to the longitudinal extension of the needle 1. The penetrating tip 4 is designed with a substantially point-shaped edge 8 to initially prick the membrane when the membrane is penetrated. The outer edges 19 present on the pointed end 3 in the area from the point-shaped edge 8 to a position beyond the opening 6 are rounded so that after the initial penetration the pointed end 3 will push the membrane material away rather than cutting the membrane material.

28 Claims, 6 Drawing Sheets

U.S. PATENT DOCUMENTS

| | | | |
|---|---|---|---|
| 3,064,651 A * | 11/1962 | Henderson | 604/274 |
| 3,071,135 A * | 1/1963 | Baldwin et al. | 604/274 |
| 3,308,822 A | 3/1967 | DeLuca | |
| 3,316,908 A | 5/1967 | Burke | |
| 3,340,671 A | 9/1967 | Loo | |
| 3,390,677 A | 7/1968 | Razimbaud | |
| 3,448,740 A * | 6/1969 | Figge | 604/274 |
| 3,542,240 A | 11/1970 | Solowey | |
| 3,783,895 A | 1/1974 | Weichselbaum | |
| 3,788,320 A * | 1/1974 | Dye | 604/165.04 |
| 3,822,700 A | 7/1974 | Pennington | |
| 3,938,520 A | 2/1976 | Scislowicz et al. | |
| 3,976,073 A | 8/1976 | Quick et al. | |
| 4,096,860 A | 6/1978 | McLaughlin | |
| 4,296,786 A | 10/1981 | Brignola | |
| D270,568 S | 9/1983 | Armstrong | |
| 4,490,139 A | 12/1984 | Huizenga et al. | |
| 4,516,967 A | 5/1985 | Kopfer | |
| 4,564,054 A | 1/1986 | Gustavsson | |
| 4,573,967 A | 3/1986 | Hargrove et al. | |
| 4,576,211 A | 3/1986 | Valentini et al. | |
| 4,581,016 A | 4/1986 | Gettig | |
| 4,582,223 A | 4/1986 | Kobe | |
| 4,588,403 A | 5/1986 | Weiss et al. | |
| 4,600,040 A | 7/1986 | Naslund | |
| 4,623,343 A | 11/1986 | Thompson | |
| 4,629,455 A | 12/1986 | Kanno | |
| 4,632,673 A | 12/1986 | Tiitola et al. | |
| 4,636,204 A | 1/1987 | Christopherson et al. | |
| 4,673,400 A | 6/1987 | Martin | |
| 4,673,405 A | 6/1987 | Gustavsson | |
| 4,737,150 A | 4/1988 | Baeumle et al. | |
| 4,752,287 A | 6/1988 | Kurtz et al. | |
| 4,759,756 A | 7/1988 | Forman et al. | |
| 4,768,568 A | 9/1988 | Fournier et al. | |
| 4,792,329 A | 12/1988 | Schreuder | |
| 4,804,015 A | 2/1989 | Albinsson | |
| 4,808,170 A * | 2/1989 | Thornton et al. | 604/274 |
| 4,822,340 A | 4/1989 | Kamstra | |
| 4,826,492 A * | 5/1989 | Magasi | 604/274 |
| 4,834,717 A | 5/1989 | Haber et al. | |
| 4,842,585 A * | 6/1989 | Witt | 604/158 |
| 4,850,978 A | 7/1989 | Dudar et al. | |
| 4,864,717 A | 9/1989 | Baus, Jr. | |
| 4,872,494 A | 10/1989 | Coccia | |
| 4,878,897 A | 11/1989 | Katzin | |
| 4,889,529 A * | 12/1989 | Haindl | 604/274 |
| 4,898,209 A | 2/1990 | Zbed | |
| 4,909,290 A | 3/1990 | Coccia | |
| 4,932,937 A | 6/1990 | Gustavsson et al. | |
| 4,944,736 A | 7/1990 | Holtz | |
| 4,964,855 A | 10/1990 | Todd et al. | |
| 4,982,769 A | 1/1991 | Fournier et al. | |
| 4,994,048 A | 2/1991 | Metzger | |
| 4,997,083 A | 3/1991 | Loretti et al. | |
| 5,017,186 A | 5/1991 | Arnold | |
| 5,041,105 A | 8/1991 | D'Alo et al. | |
| 5,061,264 A | 10/1991 | Scarrow | |
| 5,071,413 A | 12/1991 | Utterberg | |
| 5,122,116 A | 6/1992 | Kriesel et al. | |
| 5,122,123 A | 6/1992 | Vaillancourt | |
| 5,137,524 A | 8/1992 | Lynn et al. | |
| 5,158,554 A | 10/1992 | Jepson et al. | |
| 5,176,673 A | 1/1993 | Marrucchi | |
| 5,199,947 A | 4/1993 | Lopez et al. | |
| 5,201,725 A | 4/1993 | Kling | |
| 5,207,658 A * | 5/1993 | Rosen et al. | 604/272 |
| 5,232,109 A | 8/1993 | Tirrell et al. | |
| 5,254,097 A | 10/1993 | Schock et al. | |
| 5,279,576 A | 1/1994 | Loo et al. | |
| 5,279,583 A | 1/1994 | Shober, Jr. et al. | |
| 5,279,605 A | 1/1994 | Karrasch et al. | |
| 5,308,347 A | 5/1994 | Sunago et al. | |
| 5,312,366 A | 5/1994 | Vailancourt | |
| 5,328,480 A | 7/1994 | Melker et al. | |
| 5,334,163 A | 8/1994 | Sinnett | |
| 5,356,406 A | 10/1994 | Schraga | |
| 5,385,545 A | 1/1995 | Kriesel et al. | |
| 5,385,547 A | 1/1995 | Wong et al. | |
| 5,389,085 A | 2/1995 | D'Alessio et al. | |
| 5,405,326 A | 4/1995 | Haber et al. | |
| 5,445,630 A | 8/1995 | Richmond | |
| 5,447,501 A | 9/1995 | Karlsson et al. | |
| 5,456,675 A * | 10/1995 | Wolbring et al. | 604/537 |
| 5,470,522 A | 11/1995 | Thome et al. | |
| 5,478,328 A | 12/1995 | Silverman et al. | |
| 5,478,337 A | 12/1995 | Okamoto et al. | |
| 5,492,531 A | 2/1996 | Post et al. | |
| 5,514,117 A | 5/1996 | Lynn | |
| 5,515,871 A * | 5/1996 | Bittner et al. | 128/898 |
| 5,536,259 A * | 7/1996 | Utterberg | 604/272 |
| 5,575,780 A * | 11/1996 | Saito | 604/272 |
| 5,593,028 A | 1/1997 | Haber et al. | |
| 5,613,954 A | 3/1997 | Nelson et al. | |
| 5,632,735 A | 5/1997 | Wyatt et al. | |
| 5,647,845 A | 7/1997 | Haber et al. | |
| 5,685,866 A | 11/1997 | Lopez | |
| 5,752,942 A | 5/1998 | Doyle et al. | |
| 5,766,147 A | 6/1998 | Sancoff et al. | |
| 5,766,211 A | 6/1998 | Wood et al. | |
| 5,782,872 A | 7/1998 | Muller | |
| 5,795,336 A | 8/1998 | Romano et al. | |
| 5,817,083 A | 10/1998 | Shemesh et al. | |
| 5,820,609 A | 10/1998 | Saito | |
| 5,827,262 A | 10/1998 | Neftel et al. | |
| 5,837,262 A | 11/1998 | Golubev et al. | |
| 5,875,931 A | 3/1999 | Py | |
| 5,879,345 A | 3/1999 | Aneas | |
| 5,897,526 A | 4/1999 | Vaillancourt | |
| 5,934,510 A | 8/1999 | Anderson | |
| 5,984,899 A | 11/1999 | D'Alessio et al. | |
| 6,063,068 A | 5/2000 | Fowles et al. | |
| D427,308 S | 6/2000 | Zinger | |
| 6,070,623 A | 6/2000 | Aneas | |
| 6,071,270 A | 6/2000 | Fowles et al. | |
| 6,090,091 A | 7/2000 | Fowles et al. | |
| 6,113,068 A | 9/2000 | Ryan | |
| 6,113,583 A | 9/2000 | Fowles et al. | |
| 6,142,446 A | 11/2000 | Leinsing | |
| 6,146,362 A | 11/2000 | Turnbull et al. | |
| 6,209,738 B1 | 4/2001 | Jansen et al. | |
| 6,221,065 B1 | 4/2001 | Davis | |
| 6,245,056 B1 | 6/2001 | Walker et al. | |
| D445,501 S | 7/2001 | Niedospial, Jr. | |
| 6,253,804 B1 | 7/2001 | Safabash | |
| 6,258,078 B1 | 7/2001 | Thilly | |
| 6,387,074 B1 | 5/2002 | Horppu et al. | |
| 6,453,956 B2 | 9/2002 | Safabash | |
| 6,471,674 B1 | 10/2002 | Emig et al. | |
| 6,517,523 B1 * | 2/2003 | Kaneko et al. | 604/272 |
| 6,537,263 B1 | 3/2003 | Aneas | |
| 6,571,837 B2 | 6/2003 | Jansen et al. | |
| 6,591,876 B2 | 7/2003 | Safabash | |
| 6,644,367 B1 | 11/2003 | Savage et al. | |
| 6,685,692 B2 | 2/2004 | Fathallah | |
| 6,715,520 B2 | 4/2004 | Andreasson et al. | |
| 6,761,286 B2 | 7/2004 | Py et al. | |
| D495,416 S | 8/2004 | Dimeo et al. | |
| 6,786,244 B1 | 9/2004 | Jones | |
| D506,256 S | 6/2005 | Miyoshi et al. | |
| 6,960,194 B2 | 11/2005 | Hommann et al. | |
| 7,000,806 B2 | 2/2006 | Py et al. | |
| 7,080,672 B2 | 7/2006 | Fournier et al. | |
| 7,297,140 B2 | 11/2007 | Orlu et al. | |
| D570,477 S | 6/2008 | Gallogly et al. | |
| D572,820 S | 7/2008 | Gallogly et al. | |
| D577,438 S | 9/2008 | Gallogly et al. | |
| D577,822 S | 9/2008 | Gallogly et al. | |
| D582,033 S | 12/2008 | Baxter et al. | |
| D605,755 S | 12/2009 | Baxter et al. | |
| 7,703,486 B2 | 4/2010 | Costanzo | |
| D616,984 S | 6/2010 | Gilboa | |
| 7,744,581 B2 | 6/2010 | Wallen et al. | |
| 2001/0021825 A1 | 9/2001 | Becker et al. | |
| 2001/0025671 A1 | 10/2001 | Safabash | |
| 2002/0002352 A1 | 1/2002 | Becker et al. | |
| 2002/0082586 A1 | 6/2002 | Finley et al. | |

| | | | | | |
|---|---|---|---|---|---|
| 2002/0127150 A1 | 9/2002 | Sasso | EP | 0 995 453 | 4/2000 |
| 2002/0177819 A1 | 11/2002 | Barker et al. | EP | 0995453 | 4/2000 |
| 2003/0010717 A1 | 1/2003 | Brugger et al. | EP | 1060730 | 12/2000 |
| 2003/0070726 A1 | 4/2003 | Andreasson et al. | EP | 1484073 | 12/2004 |
| 2003/0106610 A1 | 6/2003 | Roos et al. | EP | 1731128 | 12/2006 |
| 2003/0107628 A1 | 6/2003 | Fowles et al. | FR | 2 757 405 | 6/1998 |
| 2003/0199846 A1 | 10/2003 | Fowles et al. | FR | 2757405 | 6/1998 |
| 2003/0233083 A1 | 12/2003 | Houwaert et al. | FR | 2780878 | 1/2000 |
| 2004/0116858 A1 | 6/2004 | Heinz et al. | GB | 1579065 | 11/1980 |
| 2004/0199139 A1 | 10/2004 | Fowles et al. | JP | 49-12690 | 5/1972 |
| 2004/0215147 A1 | 10/2004 | Wessman et al. | JP | 288664 | 7/1990 |
| 2005/0215977 A1 * | 9/2005 | Uschold .................. 604/506 | JP | 3030963 | 8/1996 |
| 2006/0025747 A1 | 2/2006 | Sullivan et al. | JP | 2000167022 | 6/2000 |
| 2006/0106360 A1 | 5/2006 | Wong | JP | 2001505092 | 4/2001 |
| 2006/0111667 A1 | 5/2006 | Matsuura et al. | JP | 2001293085 | 10/2001 |
| 2006/0157984 A1 | 7/2006 | Rome et al. | TW | 482670 | 4/2002 |
| 2006/0186045 A1 | 8/2006 | Jensen et al. | WO | WO 84/04672 | 12/1984 |
| 2007/0021725 A1 * | 1/2007 | Villette .................. 604/272 | WO | WO 84/04673 | 12/1984 |
| 2007/0060841 A1 | 3/2007 | Henshaw | WO | WO 90/03536 | 4/1990 |
| 2007/0088313 A1 | 4/2007 | Zinger et al. | WO | WO 98/19724 | 5/1998 |
| 2007/0106244 A1 | 5/2007 | Mosler et al. | WO | WO 99/27886 | 6/1999 |
| 2007/0179441 A1 | 8/2007 | Chevallier | WO | WO 99/62578 | 12/1999 |
| 2007/0270759 A1 | 11/2007 | Pessin | WO | WO 00/05292 | 2/2000 |
| 2007/0270778 A9 | 11/2007 | Zinger et al. | WO | WO 00/35517 | 6/2000 |
| 2008/0045919 A1 | 2/2008 | Jakob et al. | WO | WO 01/80928 | 11/2001 |
| 2008/0103453 A1 | 5/2008 | Liversidge | WO | WO 02/02048 | 1/2002 |
| 2008/0103485 A1 | 5/2008 | Kruger | WO | WO 02/11794 | 2/2002 |
| 2008/0172039 A1 | 7/2008 | Raines | WO | WO 02/064077 | 8/2002 |
| 2008/0223484 A1 | 9/2008 | Horppu | WO | WO 02/076540 | 10/2002 |
| 2008/0287920 A1 | 11/2008 | Fangrow et al. | WO | WO 2005/074860 | 8/2005 |
| 2008/0312634 A1 | 12/2008 | Helmerson et al. | WO | WO 2006/082350 | 8/2006 |
| 2009/0254042 A1 | 10/2009 | Gratwohl et al. | WO | WO 2006/083333 | 8/2006 |
| 2010/0137827 A1 | 6/2010 | Warren et al. | WO | WO 2008/115102 | 9/2008 |
| 2010/0204671 A1 | 8/2010 | Kraushaar et al. | WO | WO 2006/138184 | 12/2009 |
| 2010/0243099 A1 | 9/2010 | Yodfat | | | |

FOREIGN PATENT DOCUMENTS

| | | |
|---|---|---|
| DE | 2 00 519 | 10/1971 |
| DE | 2005519 | 10/1979 |
| EP | 0255025 | 2/1988 |
| EP | 0259582 | 3/1988 |
| EP | 0285424 | 10/1988 |
| EP | 0311787 | 4/1989 |
| EP | 0376629 | 7/1990 |
| EP | 0803267 | 10/1997 |
| EP | 0 819 442 | 1/1998 |
| EP | 0819442 | 1/1998 |

OTHER PUBLICATIONS

Japan Application No. 2003-583539; Official Action dated May 1, 2009 (3 pages).

Japan Application No. 2003-577789, Official Action dated Feb. 24, 2009 (4 pages).

International Search Report, PCT/EP2008/067535 dated Oct. 13, 2009 (3 pages).

International Search Report, PCT/EP2008/067522 dated Aug. 12, 2009. (2 pages).

* cited by examiner

NEEDLE FOR PENETRATING A MEMBRANE

CROSS REFERENCE TO RELATED APPLICATIONS

This application is a National Stage application under 35 U.S.C. §371 and claims the benefit under 35 U.S.C. §119(a) of International Application No. PCT/SE2004/000070 having an International Filing Date of Jan. 21, 2004, which claims the benefit of priority of Swedish Application Serial Number 0300155-9, filed Jan. 21, 2003, and U.S. Provisional Application Ser. No. 60/441,098, filed Jan. 21, 2003, all of which are incorporated herein in their entireties for all purposes.

FIELD OF THE INVENTION

The present invention relates to a needle for penetrating a membrane in accordance with the preamble of claim 1, an arrangement for transferring a liquid in accordance with the preamble of claim 21, a needle for penetrating a membrane in accordance with the preamble of claim 41 and a method for manufacturing a needle for penetrating a membrane in accordance with the preamble of claim 45.

The invention is applicable in several different technical fields of use when a membrane is penetrated, but hereinafter for illuminating, but not in any way restricting, the invention, the use when a membrane is penetrated for transferring a liquid, such as a medical substance, from a needle to a container which is sealed by the membrane or for transferring a liquid from the container to the needle, by means of the needle, will be described.

BACKGROUND OF THE INVENTION

Known needles for suction and injection of medical substances, which needles have a flow direction which is substantially parallel to the longitudinal extension of the needle, i.e. the liquid flows out from or into the needle in a main direction which is substantially parallel to the longitudinal centre line of the needle, are primarily used for injection of pharmaceutical preparations into a patient or for drawing of blood from a patient. In such cases, the needle penetrates the skin and the tissues directly under the skin and there is a strong-felt desire that the penetration may be performed while causing as little pain as possible for the patient. For this reason, the needles are designed to require as small a force as possible when the skin is penetrated and this may be achieved by the needle being ground so that the penetrating tip of the needle has sharp edges which cut an incision in the skin, through which incision the needle is inserted into the body of the patient.

Traditionally, needles of the type discussed above are also used for penetrating a membrane when medical substances are handled. Such membranes are frequently used in medical systems, for example as a seal of a container, such as medicine bottles or similar. In this connection, the needle has two functions; the needle shall penetrate the membrane, and the needle shall transport the substance. However, these needles have important drawbacks due to the fact that sharp edges of the tip of the needle may release particles from the membrane. This effect is called "coring" and is primarily initiated from sharp inner edges of the lumen of the needle. A core from the membrane, made of rubber for instance, could be produced when the needle penetrates the membrane. These cores or particles may be carried by the needle and contaminate the substance transported via the needle. Further problems arise as a consequence of the fact that the needle leaves a cut in the membrane when the membrane is penetrated, which cut has an extension corresponding to substantially the width of the edge of the needle. One or more such cuts of the membrane may result in the membrane not being able to fit tightly around the needle and, thus, leakage may arise. When medical substances are handled, it is often an absolute condition that leakage does not arise, since in the case of a leakage, the substance may be contaminated and/or spread to the environment. Furthermore, after several penetrations, parts of the membrane may be released, i.e. may be cut away, from the membrane and contaminate the current substance.

Some known needles have been developed taking into account the aspect of avoiding coring from a sharp inner edge of the lumen of the needle by mechanical blasting treatment thereof. However, since the needle must have a sharp outer edge on the tip of the needle to obtain good penetration properties as discussed above, and the needles are mass-produced, the needles are manufactured to obtain the best penetration and cutting properties at the expense of the anti-coring properties, i.e. it is not possible to blast the outermost part of the tip because in that case the cutting properties of the needle are impaired.

THE OBJECT OF THE INVENTION AND SUMMARY OF THE INVENTION

A first object of the present invention is to provide a needle of the kind defined in the introduction, which needle will reduce at least one of the drawbacks discussed above of already known such needles to a substantial extent, i.e. a needle which reduces the risk that a leakage arises and/or that particles from the membrane are released.

This object is attained according to the invention by a needle according to appended claim 1.

Due to the fact that the penetrating tip is designed with a substantially point-shaped edge to initially prick the membrane when the membrane is penetrated and that the outer edges present on the pointed end in the area between the point-shaped edge and a position beyond the opening are rounded so that after the initial penetration the pointed end will push the membrane material away rather than cutting the membrane material, ideally, a point-shaped hole without cut cuts of the membrane will be obtained when the membrane is penetrated. The absence of cut cuts of the membrane reduces the risk that leakage arises and that parts of the membrane will be removed when the membrane is penetrated. Furthermore, the rounded outer edges of the pointed end, i.e. a dulled tip, enable the needle tip to slide on the membrane to a penetration hole which originates from a previous penetration, without cutting the membrane, when penetration of the membrane is repeated, thereby causing the needle to be self-centring and to penetrate the membrane through the already existent hole, which even more reduces the risk that leakage arises and that parts of the membrane will be removed when the membrane is penetrated.

According to a preferred embodiment of the needle according to the invention the inner edge of the opening is rounded. Such a rounded inner edge further decrease the problem of coring membrane material when the needle penetrates a membrane.

According to another preferred embodiment of the needle according to the invention the penetrating tip is designed with a cross section having a symmetry causing at least three substantially equally sized forces in different directions which are radial to the longitudinal centre lines of the needle and which forces counteract each other so that the needle will tend not to deviate from the initial penetration direction when the needle penetrates a membrane. The provision of such a symmetric cross section of the penetrating tip enables the needle to follow the initial penetration direction during penetration, i.e. the needle becomes self-centring, and, thus the risk of releasing material from the membrane is decreased.

According to another preferred embodiment of the needle according to the invention, preferably in combination with the cross section discussed above, the penetrating tip is arranged to lie substantially on the longitudinal centre line of the needle. Hereby, the needle may impact the same point of the membrane in every penetration even in the case when the needle is rotated about its longitudinal axis between penetration occasions and the needle becomes self-centring, and a favourable load distribution on the membrane is obtained during penetration thereof, thereby reducing the risk of the membrane cracking adjacent to the penetration hole. Furthermore, the transport of membrane material into the needle through the opening of the needle is further obstructed.

A second object of the present invention is to provide an arrangement of the kind defined in the introduction, for transferring a liquid, in which arrangement the risk of contaminating the liquid and/or spreading the liquid to the environment has been reduced to a substantial extent.

This object is attained according to the invention by an arrangement according to appended claim 21.

The invention also relates to a needle according to claim 41. Provision of such a symmetric cross section of the penetrating tip enabling the needle to follow the initial penetration direction during the penetration and, thus, the risk of releasing material from the membrane is decreased.

According to another preferred embodiment of the needle according to claim 41, the penetrating tip is arranged to lie substantially on the longitudinal centre line of the needle. Hereby, the needle becomes even more self-centring and a favourable load distribution on the membrane is obtained during penetration thereof, reducing the risk of the membrane cracking adjacent to the penetration hole. Furthermore, the transport of membrane material into the needle through the opening of the needle is further obstructed.

A further object of the present invention is to provide a method enabling that a needle according to the invention for penetrating a membrane may be manufactured in a rational way and at a low cost.

This object is attained according to the invention by a method according to appended claim 45.

BRIEF DESCRIPTION OF THE DRAWINGS

Hereafter, preferred embodiments of the invention will be described by way of example only and with reference to the attached drawings.

In the drawings.

DETAILED DESCRIPTION OF PREFERRED EMBODIMENTS OF THE INVENTION

Figure 1:
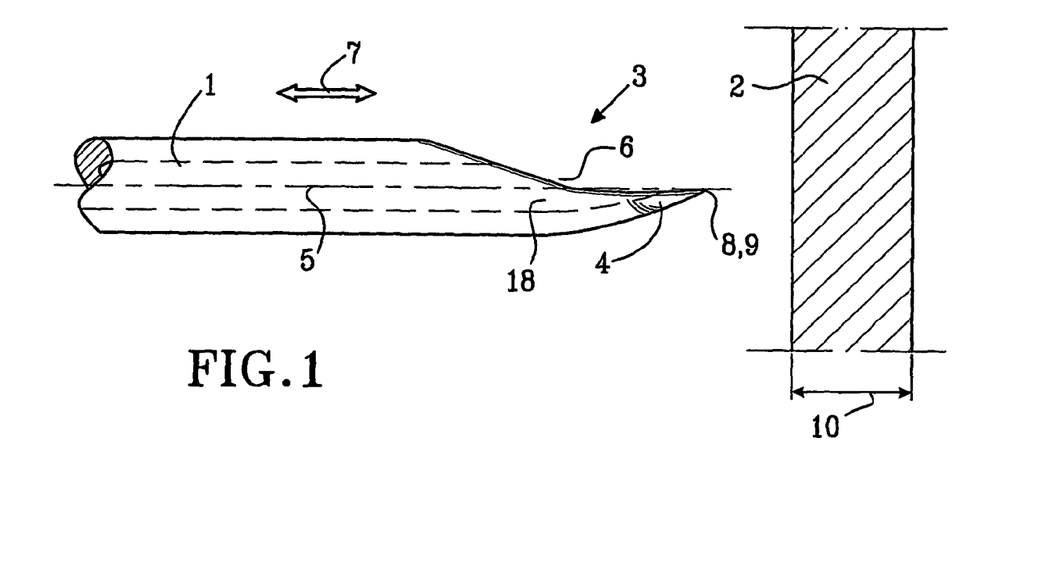
FIG. 1 is an elevational view of a part of a needle according to the invention together with a schematic membrane.
Figure 2:
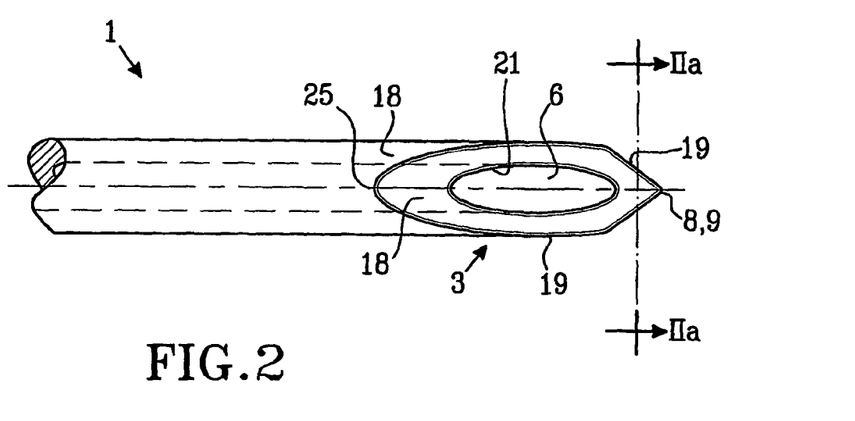
FIG. 2 is a view from above of the needle in FIG. 1.

In FIGS. 1 and 2, a needle 1 for penetrating a membrane 2 is illustrated. The needle 1 has a pointed end 3 provided with a penetrating tip 4. The outermost portion of the penetrating tip 4 is arranged to lie substantially on the longitudinal centre line 5 of the needle 1, i.e. the outermost portion is located on or very close to the centre line 5. Since the tip 4 is centred relative to the needle 1, the characteristics of the needle become independent or at least less dependent on how the needle is rotated about its longitudinal centre line 5 when a membrane 2 is penetrated. In other words, the penetrating tip 4 will impact substantially the same point on the membrane when the membrane is repeatedly penetrated even in the case when the needle is rotated about its longitudinal axis between penetration occasions. This means that the needle will always impact the membrane in the centre of the needle-membrane system resulting in a favourable load distribution on the membrane during penetration thereof, thereby reducing the risk of the membrane cracking adjacent to the penetration hole. Furthermore, in addition to the advantages already described the transport of membrane material into the needle is further obstructed.

Furthermore, the pointed end is provided with an opening 6 for letting a liquid in and/or out in a main direction 7 which is substantially parallel to the longitudinal extension of the needle 1. Such a flow direction in the forward direction is an absolute necessity in many medical systems where the needle is included, for avoiding flushing against other adjacent equipment, where otherwise the function of such equipment may be affected by the liquid in an undesirable way. Furthermore, such a flow direction in the forward direction may also enhance mixing of the current drug, such as for example a powdered substance. Although the opening 6 is arranged on substantially one and the same half of the cross section of the needle, and on the upper side of the longitudinal centre line of the needle 5 such as illustrated in FIG. 1, primarily for reasons associated with the manufacturing of the needle, it would be possible to locate one or more openings in other positions relative to the cross section of the needle 1, while maintaining the desired main direction of the flow.

The opening 6, which is located in the pointed end 3 of the needle 1, is intended to enable a liquid to be transferred to or from the needle 1. For example, the needle 1 may be inserted through a membrane which constitutes a seal of a container, such as a medicine bottle, for drawing the contents in the container up and then, in a similar way, the needle may penetrate a second membrane of a second container, such as an infusion bag, for transferring the contents previously drawn up to this second container.

The penetrating tip 4 of the needle 1 according to the invention is designed with a substantially point-shaped edge 8 to initially prick a membrane when the membrane is penetrated. Furthermore, the outer edges 19 present on the pointed end 3 in the area between the point-shaped edge 8 and a position 25 beyond the opening 6 are rounded to ensure that, after the initial penetration, the pointed end 3 will push the membrane material away rather than cutting the membrane material when the membrane is penetrated.

Figure 2A:
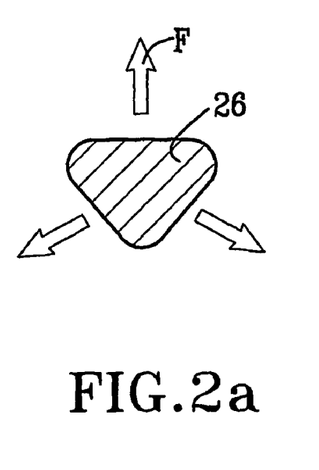
FIG. 2a is a sectional view of the penetrating tip of the needle in FIG. 2.

In FIG. 2*a* an example of a possible cross section of the outermost penetrating tip 4 is illustrated. Although the penetrating tip 4 is illustrated in FIG. 2*a* with a triangular cross section with rounded corners, other symmetries are possible such as a substantially circular cross section. The triangular symmetry gives rise to three substantially equally sized forces affecting the membrane in different directions and radial to the longitudinal extension of the needle. Since the forces counteract each other, the needle will act in a self-centring way during penetration of the membrane.

The pointed end 3 has suitably a shape substantially corresponding to a part of an imaginary cone, the tip 9 of which coincides with the substantially point-shaped edge 8. By creating a conical shape of the outermost part of the pointed end 3, preferably having a substantially triangular or circular cross section, the desired edge is obtained, which edge has the function to initially prick the membrane and, when penetration continues, the pointed end 3 will push the membrane material away, primarily in directions substantially perpendicular to the longitudinal extension of the needle, instead of cutting the membrane material, such as usual, when the subsequent part of the needle passes through the membrane. This means that, instead of cutting the membrane, the elasticity of the membrane is utilised to enable penetration of the membrane. Thus, the damaging of the membrane by forming a cut, having an extension the size of the diameter of the needle, as being characteristic for prior art needles, is avoided.

To achieve a pointed end 3 without cutting edges, the needle 1 may for example be ground and/or blasted and/or electrochemically polished to obtain the desired shape and surface smoothness and to remove possibly burrs located for example around the opening 6.

The invention also relates to an arrangement for transferring a liquid, comprising a membrane 2 and a needle 1 according to the invention for penetrating the membrane. The liquid may be transferred from inside the needle to a volume sealed by the membrane or in the opposite direction from the volume to the inside of the needle.

The needle according to the invention may be produced from a stainless steel, such as for example Stainless steel AISI 304, but also other material are possible, such as plastic for instance. With the exception of the pointed end 3 of the needle, the needle may be designed according to general standards, for example with an outer diameter of approximately 1.2 mm and an inner diameter of approximately 0.9 mm. In FIG. 1, the membrane 2 is also schematically illustrated, which membrane suitably is produced from a thermoplastic elastomer (TPE), though a silicone rubber is also a possible material of the membrane, and which membrane has a thickness 10 in the interval from parts of a millimeter to several millimeters, for example up to 10-15 mm or more, and preferably about 3 mm.

It is not unlikely that a needle 1 according to the invention, which has been designed so that at least in some respects it is blunt as compared to a conventional needle, requires that a larger force be used when the membrane is penetrated. However, this is not particularly critical, since the needle is not intended to penetrate directly in skin and/or tissue of a patient and, thereby, the problem of minimising pain inflicted on the patient to the greatest possible extent is not present. Instead, such as previously described, the primary aim is to minimize the damage of the membrane 2 to the greatest possible extent to thereby avoid possible leakage and contamination when the membrane is penetrated.

Figure 3:
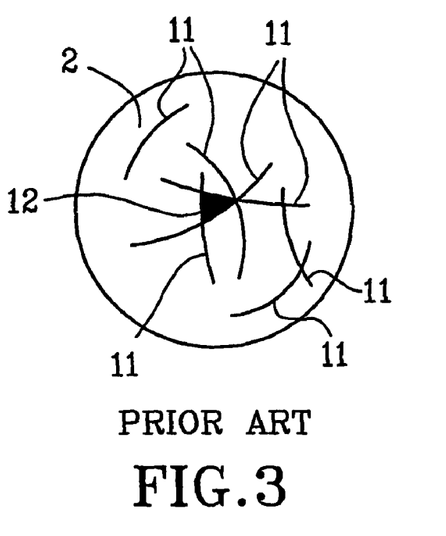
FIG. 3 is a schematic plan view of a membrane which has been penetrated by a needle designed in accordance with prior art.

In FIG. 3, a membrane is depicted which has been penetrated by a needle having a relatively wide cutting edge in accordance with prior art. A number of cuts 11 have been created when the membrane 2 was penetrated and, furthermore, it is illustrated how a part 12 of the membrane 2 thereby has been cut out and runs the risk of coming loose from the membrane and leading to contamination of the system.

Figure 4:
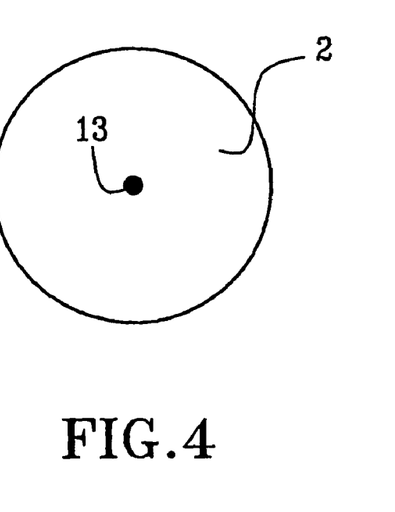
FIG. 4 is a schematic plan view of a membrane which has been penetrated by a needle designed in accordance with the invention.
Figure 4A:
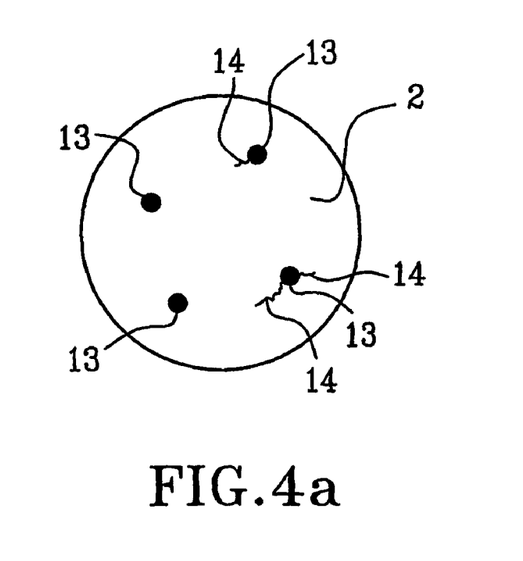
FIG. 4a is a schematic plan view of a membrane which has been penetrated at different locations by a needle designed in accordance with the invention.
Figure 5:
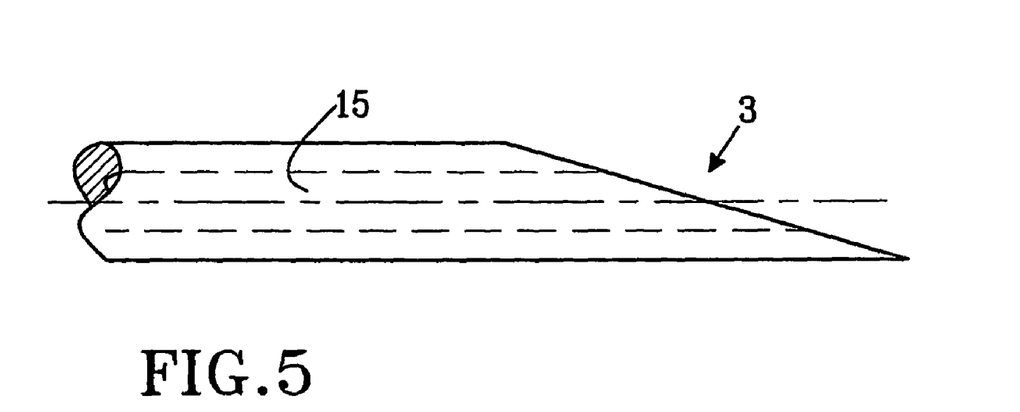
FIG. 5 is an elevational view of a part of a blank for manufacturing a needle according to the invention.
Figure 6:
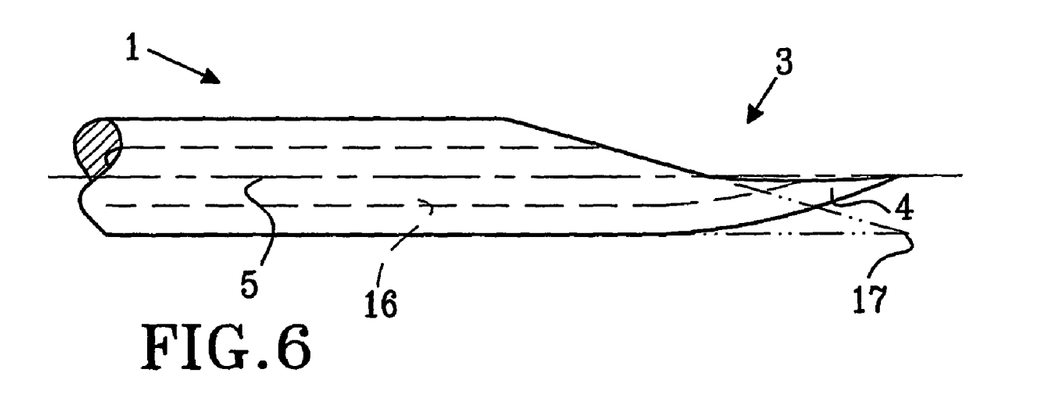
FIG. 6 is an elevational view corresponding to the view in FIG. 5 illustrating how the tip of the needle has been brought into a position so that it intersects the longitudinal centre line of the needle.
Figure 7:
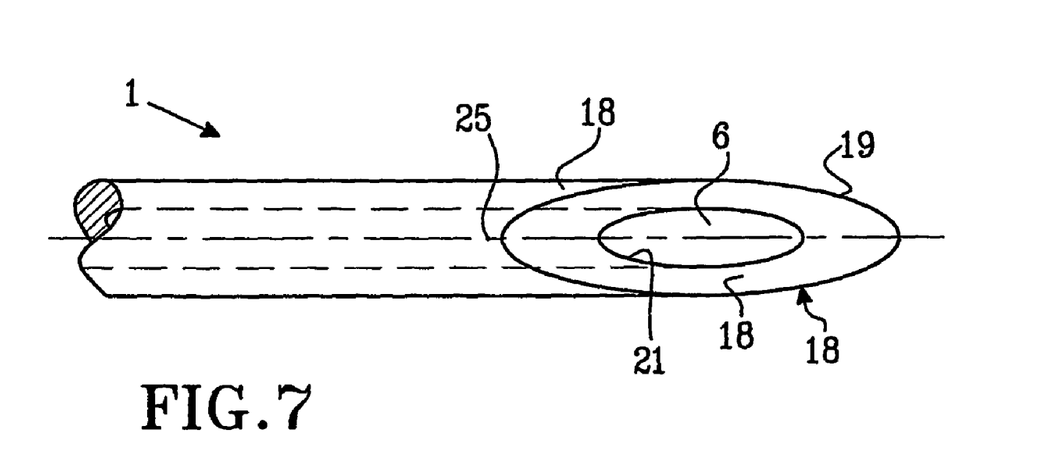
FIG. 7 is a view from above of the blank illustrated in FIG. 5.

In FIGS. 4 and 4*a*, a membrane is depicted which has been penetrated by a needle 1 according to the invention having a substantially point-shaped edge 8. In the example illustrated in 4*a*, the penetrations have been performed at different locations 13 on the membrane 2. Nevertheless, such as described above, if the point-shaped edge 8 of the penetrating tip 4 is arranged to lie substantially on the longitudinal centre line 5 of the needle 1 and the position of the centre line 5 of the needle relative to the membrane is substantially maintained between the penetrations, penetration may be performed at one and the same point 13 of the membrane, as illustrated in FIG. 4, even if the needle has been rotated about its own longitudinal axis. In the case illustrated in FIG. 4*a*, however, it is assumed that one or more penetrations have been performed at several locations 13 on the membrane 2.

If the point-shaped edge 8 is centred as described above, only one point-shaped hole 13 of the membrane 2 is formed as a consequence of several penetrations. Ideally, only such a through hole is formed when the membrane 2 is penetrated, but depending on the properties of the membrane, for example thickness, elasticity, etc., the load from the needle may also cause the membrane 2 to crack 14 adjacent to the penetration hole 13, such as illustrated for some of the penetration positions. However, it should be emphasised that these crack formations 14 are not in any way comparable to the cut cuts 11 according to FIG. 3, which necessarily arise when needles according to prior art are used. However, most often the crack formation 14 which in some cases may arise when the needle according to the invention is used is not desired, and consequently, the characteristics of the needle 1 and the membrane 2 are suitably adapted to each other so that these cracks 14 are avoided and/or delimited as regards the size to the greatest possible extent, for example by choosing a membrane material having sufficient elasticity.

In FIGS. 5-10 there is illustrated how a needle 1 may be manufactured in accordance with the method according to the invention. In a first step illustrated in FIGS. 5 and 7, a tubular blank 15 is obliquely cut, which blank 15 preferably has a circular cross section, to obtain a pointed end 3. The thus obtained pointed end 3 of the needle has an opening 6 constituting an inlet and/or outlet of a through channel 16 in the needle 1 for transport of fluid.

The pointed end 3 is then shaped so that the outermost portion of the tip, which tip is intended to constitute a penetrating tip 4 when a membrane is penetrated, lies substantially on the longitudinal centre line 5 of the tubular blank, i.e. the needle 1. For this purpose, the tip 4 is bent suitably from a position 17 located at the periphery of the needle (see FIG. 6), where the tip has a position 17 depicted by dot-dashed lines in a lower part of the needle 1, in the direction towards (upwards in FIG. 6) a position in which the tip occupies substantially the centre of a cross section of the needle. A further adjustment of the position of the tip 4 may, if so is desired, be performed in connection with the tip 4 being shaped to the desired shape in for example a subsequent grinding step.

All outer edges 19 present on the penetrating tip 4 are rounded or chamfered for forming a substantially point-shaped edge 8 according to FIGS. 1 and 2 and removing the sharp edges possibly occurring closest to the point-shaped edge 8, which edges otherwise would cut the membrane material when the membrane is penetrated. Suitable methods for removing sharp edges is to blast the pointed end 3 or to use electrochemical polishing. To give the tip 4 a basic shape and/or reduce the need of extensive surface treatment, such as blasting, the tip 4 may first be ground, for example it may be provided with a so-called back bevel cut, and thereafter the required surface treatment in the form of blasting or electrochemical polishing or any similar method is performed. Preferably all surfaces 18 and edges 19 of the pointed end 3, comprising the penetrating tip 4, in the area between the point-shaped edge 8 and a position 25 beyond the opening 6, are treated with for example blasting to shape the tip further and remove possibly sharp edges and burrs to give the needle the desired features. Furthermore, advantageously the inner edge 21, at least the rear portion of the inner edge 21 of the opening 6, is also treated with for example blasting.

Figure 8:
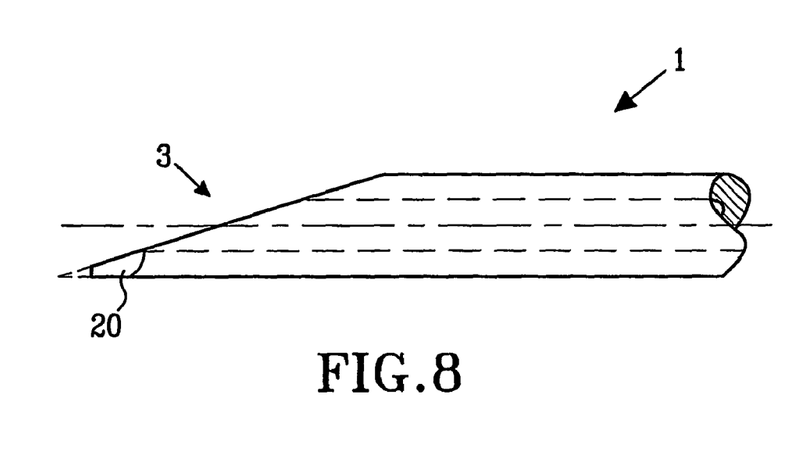
FIG. 8 is a view corresponding to the view in FIG. 6 illustrating an example of a needle according to the invention provided with a suitable cut before the needle is finally surface treated for further shaping and removing of possibly sharp edges and burrs.
Figure 9:
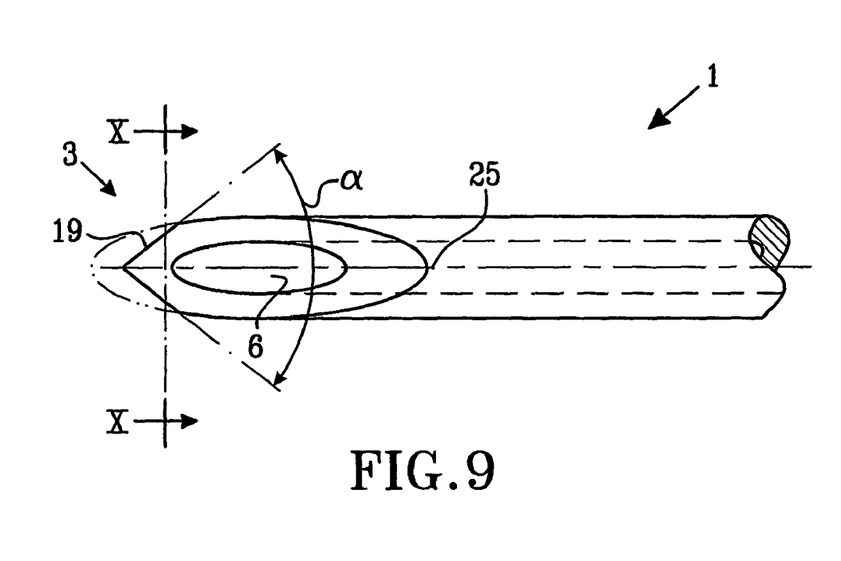
FIG. 9 is a view from above of the needle illustrated in FIG. 8.
Figure 10:
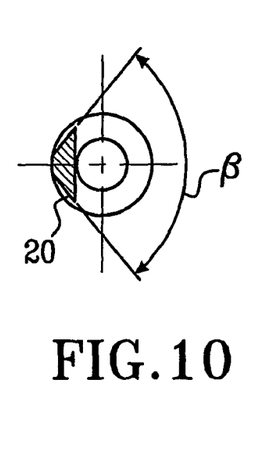
FIG. 10 is a sectional view of the needle in FIG. 9.

In FIGS. 8, 9 and 10, such a back bevel cut mentioned above which may be performed before blasting is illustrated. Furthermore, the needle is illustrated before a possible bending of the tip to the centre line, since it is often easier to grind the tip before bending thereof. The grinding is accomplished primarily on the underside 20 of the pointed end 3 of the needle 1 in such a way that, when the needle is seen from above, such as is the case in FIG. 9, a conical shape of the penetrating tip is obtained. Preferably, the pointed end 3 is provided with a first grind angle, i.e. a tip angle α, in the interval 50 to 100°, but the interval 20 to 50° is also possible, and in many cases the tip angle may be within the interval 30 to 80°. Preferably, the pointed end 3 is further provided with a second grind angle β in the interval 50 to 140°. In the illustrated example, the needle has been ground to the angles α=750 and β=100°, but it should be emphasised that the way of grinding as well as the grinding angles, during the optional grinding step, may be varied in many different ways within the scope of the invention and furthermore that it is the final shape of the needle having a point-shaped edge 8 and a rounded tip 4 without cutting edges that is the basic idea of the invention. Although a back bevel cut is preferably used to give the needle the basic form prior to the rounding of the needle, other grinding operations providing the needle with other cuts such as for example a lancet bevel cut are also possible.

However, it is also possible to obtain the desired angles and/or cross section of the pointed end by a non-cutting process, such as forging, hammering or a similar method. Such a process may be used also to bring the penetrating tip 4 and the point-shaped edge 8 to the desired positions, for example in such a way that the point-shaped edge 8 is situated substantially on the longitudinal centre line 5 of the needle 1. Such a process may be used instead of grinding the pointed end or in combination with a grinding operation. After the non-cutting process, all outer edges 19 and/or inner edges 21 present on the pointed end 4 may be rounded for further forming a substantially point-shaped edge 8 and/or removing the sharp edges possibly occurring closest to the point-shaped edge 8 by blasting or electrochemical polishing, as previously described. However, in some cases, the performed non-cutting process itself is sufficient to obtain the requisite rounded edges of the pointed end, at least in the outermost region of the needle, i.e. on the penetrating tip 4.

Figure 11:
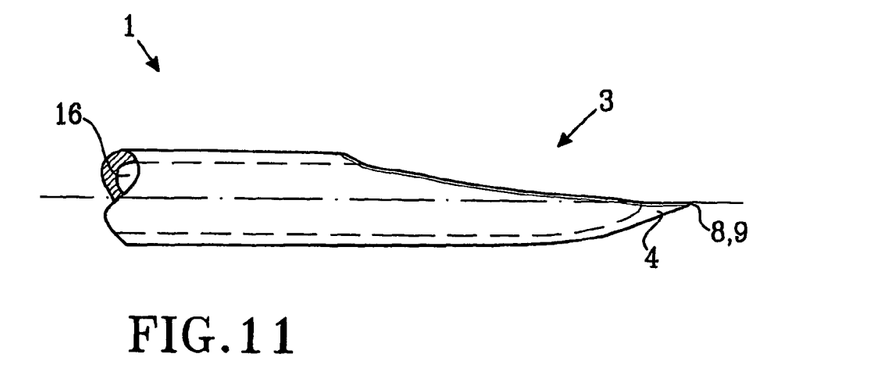
FIG. 11 is a elevational view of a variant of a needle according to the invention.
Figure 12:
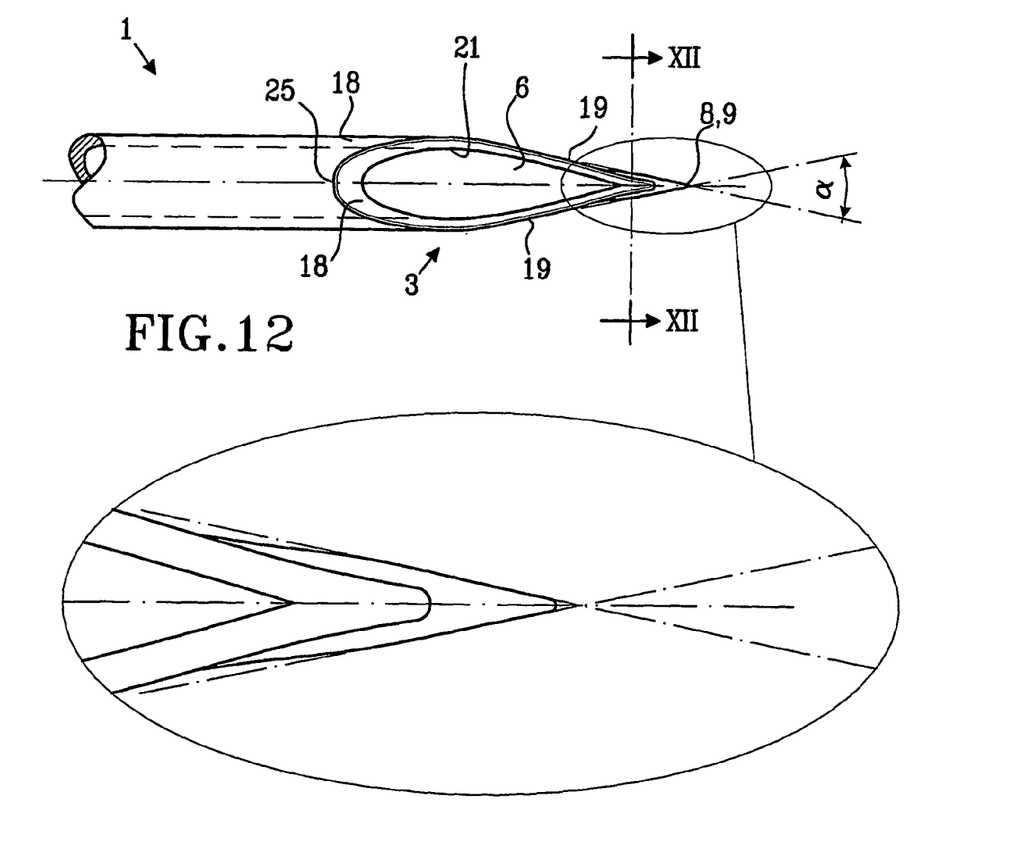
FIG. 12 is a view from above of the needle in FIG. 11.
Figure 12A:
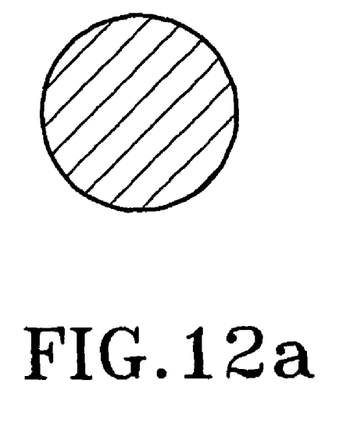
FIG. 12a is a sectional view of the penetrating tip of the needle in FIG. 12 showing a possible cross section.
Figure 12B:
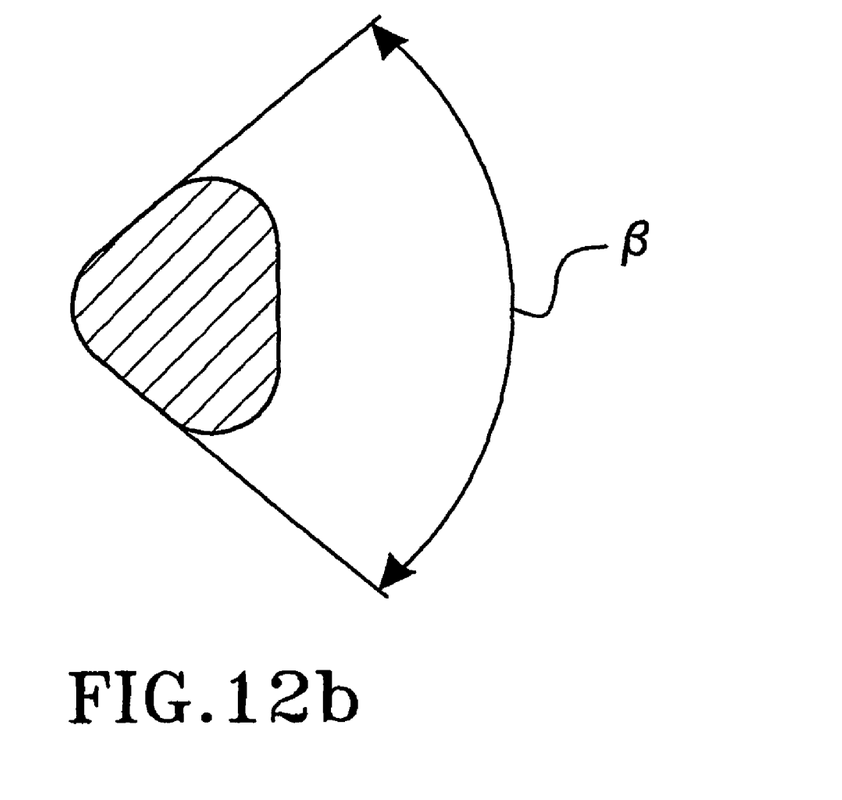
FIG. 12b is a sectional view of the penetrating tip of the needle in FIG. 12 showing a variant of the cross section.

In FIGS. 11 and 12 a variant of the needle according to the invention is illustrated. The needle is manufactured from a tubular blank which is obliquely cut to obtain a pointed end 3. Preferably, the blank has a circular cross section. The thus obtained pointed end 3 of the needle has an opening 6 constituting an inlet and/or outlet of a through channel 16 in the needle 1 for transport of fluid. The pointed end 3 is then shaped by for example hammering so that the penetrating tip 4 obtains the desired shape. The thus hammered needle is preferably provided with a basic shape having a tip angle α in the interval 20° to 100°, and more preferably the tip angle α is in the interval 30° to 80°. Furthermore, the needle may be provided with a basic shape having a rear angle β (corresponding to the second grind angle mentioned above) in the interval 50° to 140° as illustrated in FIG. 12b. As an example, the rear angle β may be approximately 100°. In FIG. 12a the cross section is substantially circular and thus, there is no rear angel. In other respects the features described in connection with the embodiment illustrated in FIGS. 1 and 2 are applicable to this embodiment too, and same reference numerals denote same or corresponding parts of the needle.

It is emphasised that the needle according to the invention, the arrangement for transferring a liquid according to the invention and the method according to the invention are not limited by the embodiments of the invention described above, but only by the scope of the following claims. Once the idea of the invention is known, several modifications within the scope of the invention could then be obvious to a man skilled in the current technical field.

The invention claimed is:

1. A membrane penetrating needle for repeatedly penetrating a membrane, having a pointed end provided with a blunt penetrating tip and with an opening for letting a liquid in and/or out in a main direction which is substantially parallel to the longitudinal extension of the needle, wherein the blunt penetrating tip is designed with a rounded point to initially prick a membrane when the membrane is penetrated and that the outer edges present on the pointed end in the area from the rounded point to a position beyond the opening are rounded so that after the initial penetration the pointed end will push the membrane material away rather than cutting the membrane material; wherein the rounded point is arranged to lie substantially on a longitudinal centre line of the needle when viewed along the longitudinal centre line of the needle, and wherein the cross section of the penetrating tip of said membrane penetrating needle is substantially triangular with rounded corners and has a symmetry causing at least three substantially equally sized forces (F) in different directions which are radial to the longitudinal centre line of the needle and which forces counteract each other so that the needle will tend not to deviate from the initial penetration direction when the needle penetrates a membrane.

2. A membrane penetrating needle according to claim 1, wherein the inner edge of the opening is rounded.

3. A membrane penetrating needle according to claim 1, wherein the cross section of the proximal end of the needle is substantially circular.

4. A membrane penetrating needle according to claim 1, wherein the pointed end has a shape substantially corresponding to a part of an imaginary cone, the tip of which coincides with the rounded point.

5. A membrane penetrating needle according to claim 1, wherein the opening is arranged on one and the same half of a cross section of the needle.

6. A membrane penetrating needle according to claim 1, wherein the pointed end is provided with a basic shape in accordance with a lancet bevel cut.

7. A membrane penetrating needle according to claim 1, wherein the pointed end is provided with a basic shape in accordance with a back bevel cut.

8. A membrane penetrating needle according to claim 7, wherein the back bevel cut has a tip angle ($\alpha$) in the interval 20° to 50°.

9. A membrane penetrating needle according to claim 7, wherein the back bevel cut has a tip angle ($\alpha$) in the interval 50° to 100°.

10. A membrane penetrating needle according to claim 7, wherein the back bevel cut has a tip angle ($\alpha$) in the interval 30° to 80°.

11. A membrane penetrating needle according to claim 10, wherein the tip angle ($\alpha$) is approximately 75°.

12. A membrane penetrating needle according to claim 7, wherein the back bevel cut has a second grind angle ($\beta$) in the interval 50° to 140°.

13. A membrane penetrating needle according to claim 12, wherein the second grind angle ($\beta$) is approximately 100°.

14. A membrane penetrating needle according to claim 1, wherein the needle is provided with a tip angle ($\beta$) in the interval 20° to 100°.

15. A membrane penetrating needle according to claim 14, wherein the tip angle ($\alpha$) is in the interval 30° to 80°.

16. A membrane penetrating needle according to claim 1, wherein the needle is provided with a rear angle ($\beta$) in the interval 50° to 140°.

17. A membrane penetrating needle according to claim 16, wherein the rear angle ($\beta$) is approximately 100°.

18. A membrane penetrating needle for repeatedly penetrating a membrane, said needle having a pointed end provided with a blunt penetrating tip and with an opening for letting a liquid in and/or out in a main direction which is substantially parallel to the longitudinal extension of the needle, wherein the point of the blunt penetrating tip is rounded and arranged to lie substantially on the longitudinal centre line of the needle when viewed along the longitudinal centre line of the needle, and the blunt penetrating tip is designed with a cross section being substantially triangular with rounded corners causing at least three substantially equally sized forces (F) in different directions which are radial to the longitudinal centre line of the needle and which forces counteract each other so that the needle will tend not to deviate from the initial penetration direction when the needle penetrates a membrane.

19. A membrane penetrating needle according to claim 18, wherein the cross section of the proximal end of the needle is substantially circular.

20. A membrane penetrating needle according to claim 1, wherein the rounded point of the blunt penetrating tip is arranged to lie substantially on the longitudinal centre line of the needle.

21. A membrane penetrating needle according to claim 1, wherein the pointed end has a shape substantially corresponding to a part of an imaginary cone, the tip of which coincides with the rounded point.

22. A membrane penetrating needle according to claim 1, wherein the pointed end has a shape substantially corresponding to a part of an imaginary cone, the tip of which coincides with the rounded point.

23. A membrane penetrating needle according to claim 1, wherein the opening is arranged on one and the same half of a cross section of the needle.

24. A membrane penetrating needle according to claim 1, wherein the pointed end is provided with a basic shape in accordance with a lancet bevel cut.

25. A membrane penetrating needle according to claim 1, wherein the pointed end is provided with a basic shape in accordance with a back bevel cut.

26. A membrane penetrating needle according to claim 1, wherein the back bevel cut has a second grind angle ($\beta$) in the interval 50° to 140°.

27. A membrane penetrating needle according to claim 1, wherein the needle is provided with a tip angle ($\alpha$) in the interval 20° to 100°.

28. A membrane penetrating needle according to claim 1, wherein the needle is provided with a rear angle ($\beta$) in the interval 50° to 140°.

* * * * *